United States Patent [19]

Lenz

[11] 4,013,644
[45] Mar. 22, 1977

[54] [8 α(E), 13aβ]-5,8,13,13a-TETRAHYDRO-2,3,10,11-TETRAMETHOXY-8-(2-PHENYLETHENYL)-6H-DIBENZO[a,g]QUINOLIZINES AND INTERMEDIATES THERETO

[75] Inventor: George R. Lenz, Glenview, Ill.

[73] Assignee: G. D. Searle & Co., Chicago, Ill.

[22] Filed: Mar. 15, 1976

[21] Appl. No.: 666,803

[52] U.S. Cl. .................. 260/240 D; 260/289 A; 260/240 AL; 424/258
[51] Int. Cl.[2] ........................................ C07D 215/14
[58] Field of Search ..... 260/240 D, 289 A, 240 AL

[56] References Cited

UNITED STATES PATENTS 3,370,063  2/1968  Suh ................................ 260/240 D

OTHER PUBLICATIONS

Kametani et al., J. C. S. Perkins I, 1974 (14) pp. 1712–1714.

*Primary Examiner*—Arthur P. Demers
*Attorney, Agent, or Firm*—John M. Brown

[57] ABSTRACT

Preparation of antifungal [8α(E),13aβ]-5,8,13,13a-tetrahydro-2,3,10,11-tetramethoxy-8-(2-phenylethenyl)-6H-dibenzo[a,g]quinolizines is disclosed.

3 Claims, No Drawings

[8 α(E), 13aβ]-5,8,13,13a-TETRAHYDRO-2,3,10,11-TETRAMETHOXY-8-(2-PHENYLETHENYL)-6H-DIBENZO[a,g]QUINOLIZINES AND INTERMEDIATES THERETO

This invention relates to [8α(E),13aβ]-5,8,13,13a-tetrahydro-2,3,10,11-tetramethoxy-8-(2-phenylethenyl)-6H-dibenzo[a,g]quinolizines and intermediates thereto. More particularly, this invention provides new, useful, and unobvious chemical compounds of the formula

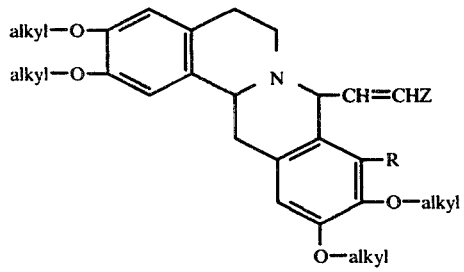

wherein R represents hydrogen or -O-alkyl and Z represents a radical of the formula

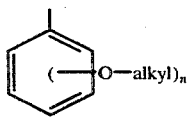

in which n represents 0 or a positive integer less than 6.

The alkyls called for by the foregoing formulas may be alike or different, but are preferably of lower order, for example, methyl, ethyl, 1-methylethyl, 1,1-dimethylethyl, propyl, 1-methylpropyl, 2-methylpropyl, 2,2-dimethylpropyl, butyl, pentyl, 4-methylpentyl, hexyl, 3-methylhexyl, heptyl, and like monovalent, saturated, acyclic, straight- or branched-chain, hydrocarbon groupings of the formula

wherein $n'$ represents a positive integer less than 8. Among these alkyls, methyl is preferred.

The number of -O-alkyl's, if any, in the radical represented by Z is not critical; but fewer than 4 in positions meta and/or para to the point of attachment of Z to the remainder of the depicted molecule are preferred.

The compounds to which this invention relates are useful by reason of their valuable biological properties. Thus, for example, they are antifungal: In a standardized test for such activity described in U.S. Pat. No. 3,668,251, the product of Example 1C hereinafter prevented the growth of *Trichophyton mentagrophytes* at 1000 mcg/ml. The well-known topical antifungal agent, undecylenic acid, was active at 100 mcg/ml in this test.

Preparation of the compounds of this invention proceeds by contacting a 3,4-dihydroisoquinoline of the formula

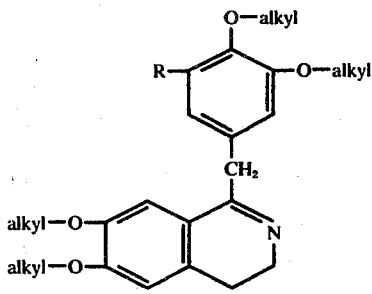

with an acid chloride or anhydride of the formulas

ZCH=CHCOCl and (ZCH=CHCO)₂O respectively, in the presence of pyridine; contacting the resultant N-acyl-1,2,3,4-tetrahydroisoquinoline

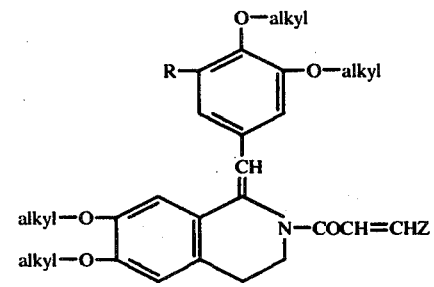

with cold concentrated sulfuric acid to effect cyclization to the corresponding 5,6-dihydrobenzo[a,g]quinolizinium salt

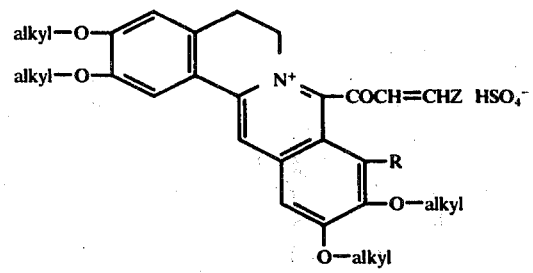

and contacting this salt with methanolic sodium tetrahydroborate(1−) — preferably but not necessarily in the presence of aqueous alkali. Throughout the foregoing formulas, the meanings of Z and R remain as originally defined.

The following examples describe in detail compounds illustrative of the present invention and methods which have been devised for their preparation. It will be apparent to those skilled in the art that many modifications, both of materials and of methods, may be practiced without departing from the purpose and intent of this disclosure. Throughout the examples hereinafter set forth, temperatures are given in degrees centigrade and relative amounts of materials in parts by weight, except as otherwise noted.

EXAMPLE 1

A. To a solution of 10 parts of 3,4-dihydro-6,7-dimethoxy-1-[(3,4-dimethoxyphenyl)methylene]isoquinoline (J. Chem. Soc., 1928, 501) in 50 parts of pyridine under nitrogen is added 15 parts of 3-phenyl-2-propenoyl chloride. The resultant mixture is stirred for 18 hours at room temperatures, then poured into 500 parts of water. The mixture thus obtained is extracted with chloroform. The chloroform extract is washed with water, dried over anhydrous sodium sulfate, and stripped of solvent by vacuum distillation. The residue is taken up in benzene; and the benzene solution is chromatographed on silica gel, using benzene and mixtures thereof with increasing amounts of ethyl acetate as developing solvent. From an eluate comprising 20% ethyl acetate in benzene, on evaporation of solvent, (1Z,2E)-1,2,3,4-tetrahydro-6,7-dimethoxy-1-[(3,4-dimethoxyphenyl)methylene]-2-(1-oxo-3-phenyl-2-propenyl)isoquinoline, melting at approximately 203°–204° is obtained as the residue. It has the formula

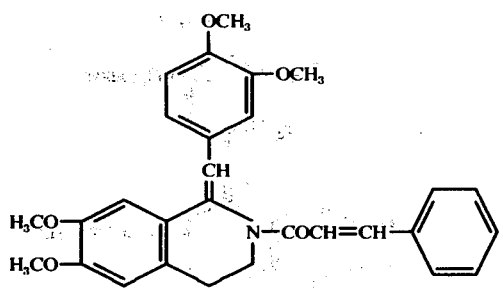

B. To 10 parts of concentrated sulfuric acid, at 0° and with vigorous stirring, is slowly added 1 part of (1Z,2E)-1,2,3,4-tetrahydro-6,7-dimethoxy-1-[(3,4-dimethoxyphenyl)methylene]-2-(1-oxo-3-phenyl-2-propenyl)isoquinoline. Stirring is continued for 10 minutes after the addition is complete, at which point 50 parts of water is introduced. The yellow precipitate which forms is (E)-5,6-dihydro-2,3,10,11-tetramethoxy-8-(2-phenylethenyl)dibenzo[a,g]quinolizinium hydrogen sulfate which, isolated by filtration, washed by slurring in boiling ethyl acetate, and dried in air, melts above 300°. It has the formula

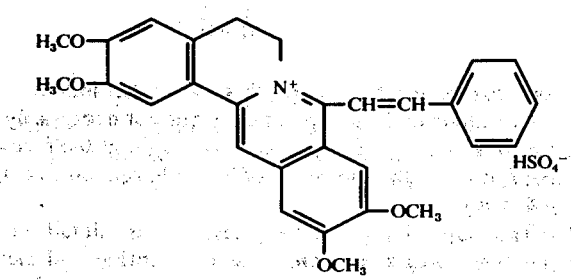

C. To a suspension of 1 part of (E)-5,6-dihydro-2,3,10,11-tetramethoxy-8-(2-phenylethenyl)-6H-dibenzo[a,g]quinolizinium hydrogen sulfate in 25 parts of methanol is added a solution of 2 parts of sodium tetrahydroborate(1−) and 2 parts of potassium hydroxide in 20 parts of water. The resultant mixture is stirred until the yellow color disappears, at which point 250 parts of water is introduced. The mixture thus obtained is extracted with dichloromethane. The extract is dried over anhydrous sodium sulfate and stripped of solvent by vacuum distillation. The residue, crystallized from methanol, affords [8α(E),13αβ]-5,8,13,13a-tetrahydro-2,3,10,11-tetramethoxy-8-(2-phenylethenyl)-6H-dibenzo[a,g]quinolizine melting at 183°–186°. The product has the formula

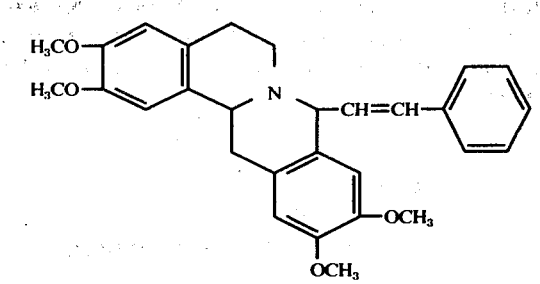

EXAMPLE 2

A. Substitution of 15 parts of 3-(4-methoxyphenyl)-2-propenoyl chloride for the 3-phenyl-2-propenoyl chloride called for in Example 1A affords, by the procedure there detailed, (1Z,2E)-1,2,3,4-tetrahydro-6,7-dimethoxy-1-[(3,4-dimethoxyphenyl)methylene]-2-[3-(4-methoxyphenyl)-1-oxo-2-propenyl]isoquinoline.

B. To 10 parts of concentrated sulfuric acid, at 0° and with vigorous stirring, is slowly added 1 part of (1Z,2E)-1,2,3,4-tetrahydro-6,7-dimethoxy-1-[(3,4-dimethoxyphenyl)methylene]-2-[3-(4-methoxyphenyl)-1-oxo-2-propenyl]isoquinoline. Stirring is continued for 10 minutes after the addition is complete, at which point 50 parts of water is mixed in. The yellow precipitate which forms is (E)-5,6-dihydro-2,3,10,11-tetramethoxy-8-[2-(4-methoxyphenyl)ethenyl]dibenzo[a,g]quinolizinium hydrogen sulfate, which is isolated by filtration, washed with water, and dried in air.

C. Substitution of 1 part of (E)-5,6-dihydro-2,3,10,11-tetramethoxy-8-[2-(4-methoxyphenyl)ethenyl]dibenzo[a,g]quinolizinium hydrogen sulfate for the (E)-5,6-dihydro-2,3,10,11-tetramethoxy-8-(2-phenylethenyl)dibenzo[a,g]quinolizinium hydrogen sulfate called for in Example 1C affords, by the procedure there detailed, [8α(E),13αβ]5,8,13,13a-tetrahydro-2,3,10,11-tetramethoxy-8-[2-(4-methoxyphenyl)ethenyl]-6H-dibenzo[a,g]quinolizine.

EXAMPLE 3

A. To a solution of 100 parts of 3-(3,4,5-trimethoxyphenyl)-2-propenoic acid in 1125 parts of benzene is added 22 parts of N,N-diethyl-1-propyne-1-amine. The resultant mixture is stirred for 2 hours, whereupon a solution of 75 parts of 3,4-dihydro-6,7-dimethoxy-1-[(3,4,5-trimethoxyphenyl)methylene]isoquinoline [Ber. deut. chem. Ges., 55, 2889 (1922)] in 200 parts of pyridine is introduced. The mixture thus obtained is stirred and heated at 65° for 3 hours, then cooled, consecutively washed with water and aqueous 5% sodium bicarbonate, dried over anhydrous sodium sulfate, and stripped of solvent by vacuum distillation. The residue is crystallized from a mixture of ethyl acetate and ether to give (1Z,2E)-1,2,3,4-tetrahydro-6,7-dimethoxy-1-[(3,4,5-trimethoxyphenyl)methylene]-2-[3-(3,4,5-trimethoxyphenyl)-1-oxo-2-propenyl]isoquinoline melting at 180°–183°.

B. Substitution of 1 part of (1Z,2E)-1,2,3,4-tetrahydro-6,7-dimethoxy-1-[(3,4,5-trimethoxyphenyl)-methylene]-2-[3-(3,4,5-trimethoxyphenyl)-1-oxo-2-propenyl]isoquinoline for the (1Z,2E)-1,2,3,4-tetrahydro-6,7-dimethoxy-1-[(3,4-dimethoxyphenyl)-methylene]-2-[3-(4-methoxyphenyl)1-oxo-2-propenyl]isoquinoline called for in Example 2B affords, by the procedure there detailed, (E)-5,6-dihydro-2,3,9,10,11-pentamethoxy-8-[2-(3,4,5-trimethoxyphenyl)-ethenyl]-dibenzo[a,g]quinolizinium hydrogen sulfate.

C. Substitution of 1 part of (E)-5,6-dihydro-2,3,9,10,11-pentamethoxy-8-[2-(3,4,5-trimethoxyphenyl)-ethenyl]dibenzo[a,g]quinolizinium hydrogen sulfate for the (E)-5,6-dihydro-2,3,10,11-tetramethoxy-8-(2-phenylethenyl)dibenzo[a,g]quinolizinium hydrogen sulfate called for in Example 1C affords, by the procedure there detailed, [8α(E),13aβ]-5,8,13,13a-tetrahydro-2,3,9,10,11-pentamethoxy 8-[2-(3,4,5-trimethoxyphenyl)ethenyl]-6H-dibenzo[a,g]quinolizine.

What is claimed is:

1. A compound of the formula

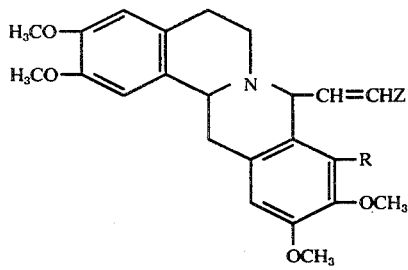

wherein Z represents phenyl optionally substituted by fewer than 4 methoxys and R represents hydrogen or methyl.

2. A compound according to claim 1 having the formula

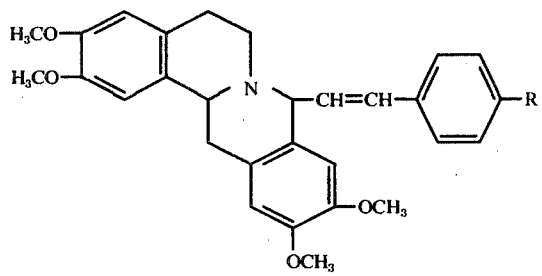

wherein R represents hydrogen or methoxy.

3. A compound according to claim 1 which is [8α(E),13aβ]-5,8,13,13a-tetrahydro-2,3,10,11-tetramethoxy-8-(2-phenylethenyl)-6H-dibenzo[a,g]quinolizine.

* * * * *